United States Patent [19]
Kerby et al.

[11] Patent Number: 5,472,596
[45] Date of Patent: Dec. 5, 1995

[54] INTEGRATED FLUID COKING PARAFFIN DEHYDROGENATION PROCESS

[75] Inventors: Michael C. Kerby; Roby Bearden, Jr.; Stephen M. Davis, all of Baton Rouge, La.

[73] Assignee: Exxon Research and Engineering Company, Florham Park, N.J.

[21] Appl. No.: 194,557

[22] Filed: Feb. 10, 1994

[51] Int. Cl.$^6$ .............................. C10G 9/28; C07C 5/327
[52] U.S. Cl. ........................... 208/127; 585/324; 585/654
[58] Field of Search ...................................... 585/654, 661, 585/662, 663; 208/127

[56] References Cited

U.S. PATENT DOCUMENTS 4,269,696  5/1981  Metrailer .................................. 208/120
4,297,202  10/1981 Blaser ....................................... 208/54
5,176,819  1/1993  Green ....................................... 208/127
5,228,981  7/1993  Olmstead et al. ....................... 208/127
5,284,574  2/1994  Chen et al. .............................. 208/127

Primary Examiner—P. Achutamurthy
Attorney, Agent, or Firm—Henry E. Naylor

[57] ABSTRACT

An integrated fluid coking/paraffin dehydrogenation process. The fluid coking unit is comprised of a fluid coker reactor and a heater with hot solids recycling between the coker reactor and the heater. A light paraffin stream is introduced into the line wherein the hot particles are recycled to the coking zone. The hot particles act to catalyze the dehydrogenation of the paraffins to olefins.

12 Claims, 1 Drawing Sheet

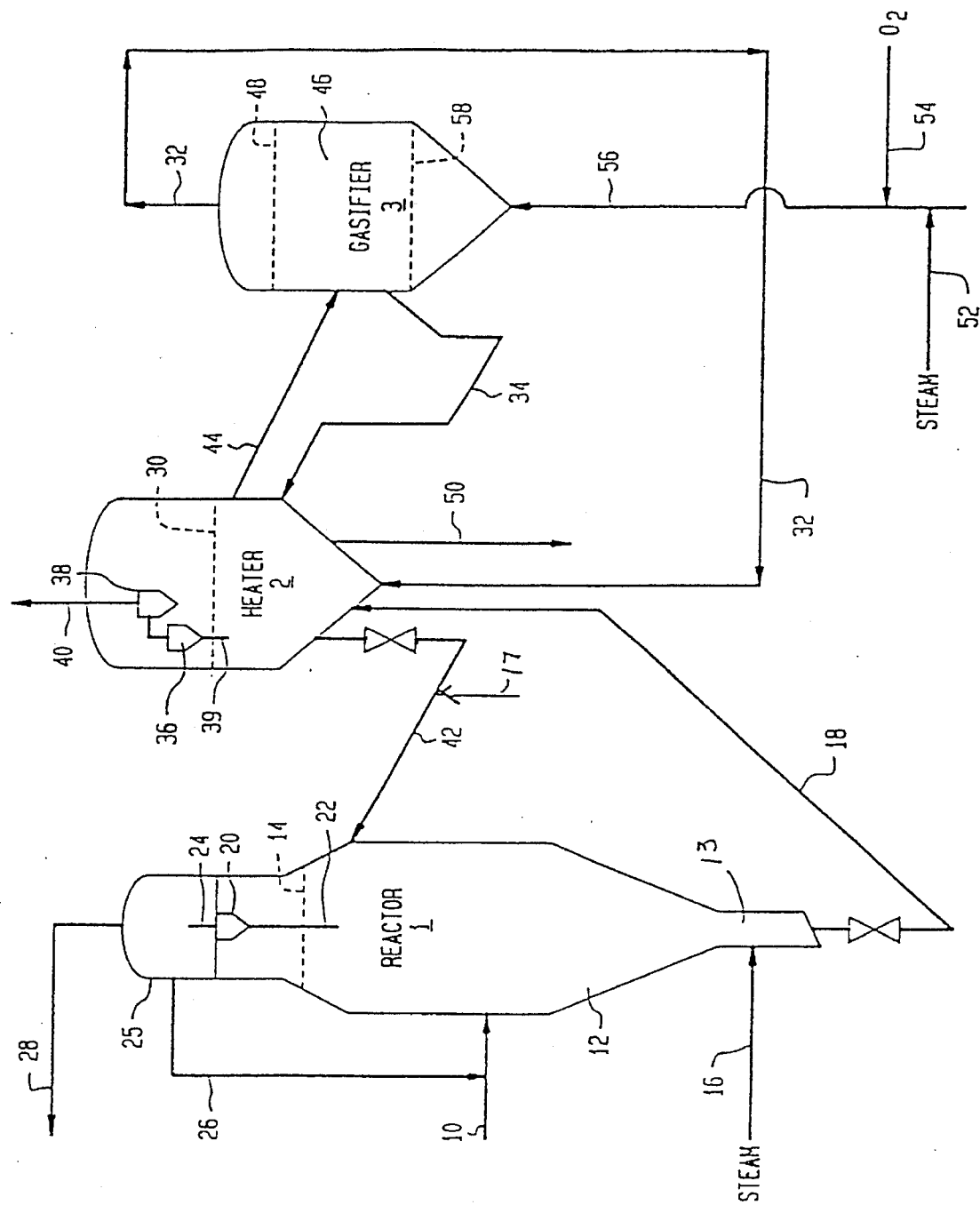

5,472,596

INTEGRATED FLUID COKING PARAFFIN DEHYDROGENATION PROCESS

FIELD OF THE INVENTION

The present invention relates to an integrated fluid coking/paraffin dehydrogenation process. The fluid coking unit is comprised of a fluid coker reactor and a heater with hot particles recycling between the coker reactor and the heater. A light paraffin stream is introduced into the line in which the hot particles are recycled to the coking zone. The hot particles act to catalyze the dehydrogenation of paraffins to olefins.

BACKGROUND OF THE INVENTION

Transportation fuels, particularly motor gasoline, contain a relatively high level of aromatic components, such as benzene. These fuels, while relatively high in octane number, are facing ever growing difficultly in meeting environmental regulations with regard to emissions. This is primarily because of their high level of aromatics. Consequently, much work is being done to develop what has become known as "low emissions fuels". An important aspect of this work involves the substitution of non-aromatic components, having a relatively high octane value, for aromatic components of the fuel.

A class of non-aromatic components having relatively high octane value, which has been proposed for the production of low emissions fuels, is oxygenates. Non-limiting examples of preferred oxygenates for fuels include the unsymmetrical dialkyl ethers, particularly methyl tert-butyl ether (MTBE), ethyl tert-butyl ether (ETBE), and tert-amylmethyl ether (TAME). Conventional methods for the manufacture of MTBE include the reaction of iso-butylene with methanol over cation-exchanged resins. This has created a significant demand for isobutylene. Furthermore, there is also a demand in the chemical industry for other low carbon number olefins.

Low carbon number olefins, for example those having 2 to 10 carbon atoms, are typically obtained by the dehydrogenation of the corresponding paraffinic hydrocarbon. One method for light paraffin dehydrogenation is the socalled oxidative dehydrogenation process where light alkanes are reacted with oxygen over a mixed metal oxide catalyst to produce a mixture of olefin, water, $CO_x$, and unreacted paraffin. While high conversions combined with high olefin selectivities can be achieved, this process has a number of disadvantages. One disadvantage is the loss of fuel value because of water and $CO_x$ formation. Another disadvantage concerns the relatively high costs of running the process. There are also problems concerning hazards associated with exothermic combustion reactions.

A more direct and preferred approach for producing low carbon number olefins, is direct dehydrogenation over a suitable catalyst to produce olefins and molecular hydrogen. This chemistry has recently received considerable interest, although high reaction temperatures in the range of 500° C. to 650° C. are required to obtain a significant equilibrium yield (e.g., 15–65%) of olefin. Moreover, under these reaction conditions light alkane hydrogenolysis to methane and ethane is a competing undesirable reaction. Most catalysts studied to date have not shown suitable selectivities for dehydrogenation versus hydrogenolysis. They have also suffered from rapid deactivation, necessitating frequent regeneration. As a consequence, the process economics have not been clearly favorable. Large incentives exist for catalysts which show relatively high selectivity for olefins and which have improved resistance to deactivation. It is also desirable that the catalyst be capable of being regenerated using relatively inexpensive procedures, such as treatment with air.

It was found by the inventors hereof that a carbonaceous catalyst will effectively catalyze the dehydrogenation of light alkanes. This is the subject of U.S. patent application Ser. No. 07/900,977, filed Jun. 18, 1992, which is incorporated herein by reference.

One source of carbonaceous material in some modern complex petroleum refineries is in fluid coking process units. In conventional fluid coking, in a process unit comprised of a coking reactor and a heater or burner, a petroleum feedstock is injected into the reactor in a coking zone comprised of a fluidized bed of hot, fine, coke particles and is distributed uniformly over the surfaces of the coke particles where it is cracked to vapors and coke. The vapors pass through a cyclone which removes most of the entrained coke particles. The vapor is then discharged into a scrubbing zone where the remaining coke particles are removed and the products cooled to condense the heavy liquids. The resulting slurry, which usually contains from about 1 to about 3 wt. % coke particles, is recycled to extinction to the coking zone.

The coke particles in the coking zone flow downwardly to a stripping zone at the base of the reactor vessel where steam removes interstitial product vapors from, or between, the coke particles, and some adsorbed liquids from the coke particles. The coke particles then flow down a stand-pipe and into a riser which moves them to a burning, or heating zone, where sufficient air is injected for burning at least a portion of the coke and heating the remainder sufficiently to satisfy the heat requirements of the coking zone where the unburned hot coke is recycled. Net coke, above that consumed in the burner, is withdrawn as product coke.

Another type of fluid coking employs three vessels: a coking reactor, a heater, and a gasifier. Coke produced in the coking reactor is withdrawn and is passed to the heater where a portion of the volatile matter is removed. The coke is then passed to the gasifier where it reacts, at elevated temperatures, with air and steam to form a mixture of carbon monoxide, carbon dioxide, methane, hydrogen, nitrogen, water vapor, and hydrogen sulfide. The gas produced in the gasifier is passed to the heater to provide part of the reactor heat requirement. The remainder of the heat is supplied by circulating coke between the gasifier and the heater. Coke is also recycled from the heater to the coking reactor to supply the heat requirements of the reactor.

There is a need in the art for producing olefins in a more cost efficient manner, especially if a cheap source of catalyst, such as coke from a fluid coking unit could be used.

SUMMARY OF THE INVENTION

In accordance with the present invention, there is provided an integrated process for converting a heavy hydrocarbonaceous chargestock to lower boiling products and for converting light paraffins to olefins. The process is performed in a fluid coking process unit comprised of a fluid coking reactor and a heater. Hot solids are recycled between the coking reactor and the heater. The fluid coking reactor contains a coking zone, a scrubbing zone located above the coking zone for collecting vapor phase products, and a stripping zone at the bottom of the coking zone for stripping hydrocarbons from solid particles passing downwardly through the coking zone where they exit and are passed to the heater. Vapor phase products are separated in the scrubbing zone. Olefins are produced by introducing a stream of $C_2$ to $C_{10}$ paraffins into the line wherein hot solids are passing from the heater to the coking reactor.

In a preferred embodiment of the present invention, the process unit is comprised of a coking reactor, a heater, and a gasifier with hot coke particles being recycled between the coking reactor and the heater and between the heater and the gasifier.

In a another preferred embodiment of the present invention, the paraffin stream which is introduced into the solid particles passing from the burner to the coking reactor are predominantly $C_2$ to $C_6$ paraffins.

In yet another preferred embodiment of the present invention, the coking zone is operated at a temperature from about 450° C. to 650° C. and at a pressure from about 0 to 150 psig.

In still another preferred embodiment of the present invention, the chargestock is selected from the group consisting of heavy and reduced petroleum crudes, petroleum atmospheric distillation bottoms, petroleum vacuum distillation bottoms, pitch, asphalt, bitumen, and liquid products derived from a coal liquefaction process.

BRIEF DESCRIPTION OF THE FIGURE

The sole FIGURE herein is a schematic flow plan of a preferred embodiment of the present invention.

DETAILED DESCRIPTION OF THE INVENTION

Suitable heavy hydrocarbonaceous feedstocks for use in the present invention include heavy hydrocarbonaceous oils, heavy and reduced petroleum crude oil; petroleum atmospheric distillation bottoms; petroleum vacuum distillation bottoms, or residuum; pitch; asphalt; bitumen; other heavy hydrocarbon residues; tar sand oil; shale oil; coal; coal slurries; liquid products derived from coal liquefaction processes, including coal liquefaction bottoms; and mixtures thereof. Such feeds will typically have a Conradson carbon content of at least 5 wt. %, generally from about 5 to 50 wt. %. As to Conradson carbon residue, see ASTM Test D189-165. Preferably, the feed is a petroleum vacuum residuum.

A typical petroleum chargestock suitable for the practice of the present invention will have the composition and properties within the ranges set forth below.

| | |
|---|---|
| Conradson Carbon | 5 to 40 wt. % |
| Sulfur | 1.5 to 8 wt. % |
| Hydrogen | 9 to 11 wt. % |
| Nitrogen | 0.2 to 2 wt. % |
| Carbon | 80 to 86 wt. % |
| Metals | 1 to 2000 wppm |
| Boiling Point | 340° C.+ to 650° C.+ |
| Specific Gravity | −10 to 35° API |

Reference is now made to the FIGURE, which shows a fluid coking process unit containing a coker reactor 1, a heater 2 and a gasifier 3. A heavy hydrocarbonaceous chargestock is passed via line 10 to coking zone 12 of coking reactor 1, which coking zone contains a fluidized bed of solid, or so-called "seed" particles, having an upper level indicated at 14. Although it is preferred that the solid particles be coke particles, they may be any other suitable refractory material. Non-limiting examples of such other suitable refractory materials are those selected from the group consisting of silica, alumina, zirconia, magnesia, or mullite, synthetically prepared or naturally occurring material such as pumice, clay, kieselguhr, diatomaceous earth, bauxite, and the like. The solids will have an average particle size of about 40 to 1000 microns, preferably from about 40 to 400 microns.

A fluidizing gas e.g. steam, is admitted at the base of coker reactor 1, through line 16, into stripping zone 13 of the coker reactor in an amount sufficient to obtain superficial fluidizing velocity. Such a velocity is typically in the range of about 0.5 to 5 ft/sec. A portion of the decomposed feed forms a fresh coke layer on the fluidized solid particles. The solids are partially stripped of fresh coke and occluded hydrocarbons in stripping zone 13 by use of said steam and are passed via line 18 to heater 2. Coke at a temperature in excess of the coking temperature, for example, at a temperature from about 40° C. to 200° C., preferably from about 65° C. to 175° C., and more preferably about 65° C. to 120° C. in excess of the actual operating temperature of the coking zone is admitted to reactor 1 by line 42 in an amount sufficient to maintain the coking temperature in the range of about 450° C. to 650° C. A stream of light paraffins is introduced into line 42 via line 17. The stream will contain a predominant amount of one or more $C_2$ to $C_{10}$ paraffins. By predominant amount we mean that at least 50 wt. % of the stream will be composed of paraffins. Preferred are $C_2$ to $C_{10}$ alkanes and substituted alkanes; alkenes and substituted alkenes; alicyclic compounds, such as cyclohexane; alkylaryl compounds, wherein the alkyl group contains from about 2 to 10 carbon atoms, such as 1-butylbenzene; and naphtheno-aromatics, such as tetrahydro-naphthalene. It is to be understood that the product stream will be comprised predominantly of olefins, diolefins, and mixtures thereof, depending on the composition of the feedstream. Preferred are $C_2$ to $C_6$ hydrocarbons, and more preferred are $C_2$ to $C_5$ hydrocarbons, particularly the alkanes and alkenes. Typical hydrocarbon streams which can be used in the practice of the present invention are petroleum refinery streams containing such components. Non-limiting examples of such refinery streams include: the $C_3$–$C_4$ stream from reforming, coking, or hydrocracking; and the $C_2$–$C_5$ stream from fluid catalytic cracking. The non-aromatic portions of the hydrocarbons are dehydrogenated by contact with the hot coke particles in line 42.

The pressure in the coking zone is maintained in the range of about 0 to 150 psig, preferably in the range of about 5 to 45 psig. Conversion products are passed through cyclone 20 of the coking reactor to remove entrained solids which are returned to the coking zone through dipleg 22. The vapors leave the cyclone through line 24, and pass into a scrubber 25 at the top of the coking reactor. If desired, a stream of heavy materials condensed in the scrubber may be recycled to the coking reactor via line 26. The coker conversion products are removed from the scrubber via line 28 for fractionation in a conventional manner. The olefins which are generated by contacting the paraffin stream with hot solids in line 42 are removed via this line 28 and recovered downstream by fractionation.

In heater 2, stripped coke from coking reactor 1 (cold coke) is introduced by line 18 to a fluid bed of hot coke having an upper level indicated at 30. The bed is partially heated by passing a fuel gas into the heater by line 32. Supplementary heat is supplied to the heater by coke circulating from gasifier 3 through line 34. The gaseous effluent of the heater, including entrained solids, passes through a cyclone which may be a first cyclone 36 and a second cyclone 38 wherein the separation of the larger entrained solids occur. The separated larger solids are returned to the heater bed via the respective cyclone diplegs 39. The heated gaseous effluent which contains entrained solids is removed from heater 2 via line 40.

As previously mentioned, hot coke is removed from the fluidized bed in heater 2 and recycled to coking reactor by line 42 to supply heat thereto. Another portion of coke is removed from heater 2 and passed via line 44 to a gasification zone 46 in gasifier 3 in which is also maintained a bed of fluidized solids to a level indicated at 48. If desired, a purged stream of coke may be removed from heater 2 by line 50.

The gasification zone is maintained at a temperature ranging from about 870° C. to 1100° C. at a pressure ranging from about 0 to 150 psig, preferably at a pressure ranging from about 25 to about 45 psig. Steam via line 52, and an oxygen-containing gas, such as air, commercial oxygen, or air enriched with oxygen by line 54, are passed via line 56 into gasifier 3. The reaction of the coke particles in the gasification zone with steam and the oxygen-containing gas produces a hydrogen and carbon monoxide-containing fuel gas. The gasified product gas, which may contain some entrained solids is removed overhead from gasifier 3 by line 32 and introduced into heater 2 to provide a portion of the required heat as previously described.

It is within the scope of the present invention to improve conversion activity by introducing an effective amount of one or more metals selected from Groups I, such as Na and K; Group IIA, such as Mg and Ca; Group VA, such as V; Group VIA, such as Cr and Mo; Group VIIA, such as Mn, and Group VIIIA, such as Fe, Co, and Ni. The groups referred to are from the Periodic Table of the Elements as published by Sargent-Welch Scientific Co., Catalog Number S-18806, 1979. Preferred are K, Ca, V, Ni, and Fe. Effective amount, as used herein, means that amount which will cause an measureable increase in conversion activity, preferably at least a 5% increase in activity, more preferably at least a 10% in activity, over the case where no such metal are added. Compounds or mixtures of compounds containing said metals can be added with the feed to the fluid coker reactor, or may be introduced as a separate stream into any of the vessels of the coking process unit.

Having thus described the present invention, and a preferred embodiment thereof, it is believed that the same will become even more apparent by reference to the following examples. It will be appreciated, however, that the examples, as well as the FIGURE hereof, are presented for illustrated purposes and should not be construed as limiting the invention.

EXAMPLES

A burner coke (90.51 wt. % C: 1.75 wt. % H; 0.051 wt. % V: 0.035 wt. % Ni; 0.013 wt. % Fe; Surface Area 1 m$^2$/g) obtained from a commercial fluid coking unit comprised of a coking reactor and a burner, and heater coke (92.46 wt. % C; 0.68 wt. % H: 0.48 wt. % V: 0.18 wt. % Ni; 0.02 wt. % Fe; Surface Area 38 m$^2$/g) obtained from a commercial fluid coking unit comprised of coking reactor, a heater, and a gasifier were placed in a fixed bed quartz reactor. Upon reaching the desired reaction temperature (650° C.) under nitrogen, iso-butane feed was admitted to the catalyst bed at 1 atm and at residence times of 1 and 5 seconds. Product samples were analyzed with a gas chromatograph and mass spectrometer. A silica-alumina material having a low surface area of about 1 m$^2$/g was used as a thermal reference for comparison purposes. The results are shown in the following table.

| Example | Comp.Ex. | 1 | 2 | 3 | 4 |
| --- | --- | --- | --- | --- | --- |
| Run Number | 4-004 | 5-158 | 4-082 | 6-002 | 4-118 |
| Catalyst | Thermal Reference | Burner Coke | Heater Coke | Burner Coke | Heater Coke |
| Temperature (°C.) | 650 | 650 | 650 | 650 | 650 |
| Residence Time (sec) | 1 | 1 | 1 | 5 | 5 |
| GHSV[1] | 1066 | 1066 | 1066 | 215 | 215 |
| Conversion (wt. %) | 13.30 | 13.73 | 20.25 | 40.44 | 51.59 |
| Yield (wt. %) | | | | | |
| H$_2$ | 0.16 | 0.20 | 0.45 | 0.40 | 1.08 |
| CO$_2$ | 0.08 | 0.11 | 0.18 | 0.89 | 0.88 |
| CH$_4$ | 1.42 | 1.17 | 1.52 | 4.74 | 5.39 |
| C$_2$H$_6$ | 0.02 | 0.02 | 0.05 | 0.32 | 0.34 |
| C$_2$H$_4$ | 0.15 | 0.00 | 0.00 | 0.00 | 0.00 |
| C$_3$H$_8$ | 0.25 | 0.24 | 0.01 | 1.23 | 0.35 |
| C$_3$H$_6$ | 3.52 | 2.99 | 2.97 | 7.08 | 5.88 |
| n-C$_4$H$_{10}$ | 0.11 | 0.01 | 0.00 | 0.27 | 0.01 |
| 1-Butene | 0.00 | 0.01 | 0.02 | 0.04 | 0.07 |
| Iso-Butylene | 7.34 | 8.79 | 14.82 | 25.06 | 35.56 |
| t-2-Butene | 0.01 | 0.00 | 0.02 | 0.04 | 0.07 |
| c-2-Butene | 0.00 | 0.00 | 0.02 | 0.04 | 0.07 |
| >C$_4$'s | 0.27 | 0.12 | 0.00 | 0.34 | 0.46 |
| Iso-Butylene Selectivity (%) | 55.2 | 64.0 | 73.2 | 62.0 | 68.9 |

[1]GHSV = gas hourly space velocity = ml of gas per hour per ml of catalyst per hour.

What is claimed is:

1. An integrated process for converting a heavy hydrocarbonaceous chargestock to lower boiling products and for converting light paraffins to olefins, said process being performed in a fluid coking process unit comprised of a fluid coking reactor and a heater, containing a heating zone, said fluid coking reactor containing a coking zone, a scrubbing zone located above the coking zone for collecting vapor phase products, and a stripping zone, at the bottom of the coking zone, for stripping hydrocarbons from solid particles passing downwardly through the coking zone, which process comprises:

(a) introducing the heavy hydrocarbonaceous chargestock having a Conradson carbon content of at least about 5 wt. %, into said coking zone containing a fluidized bed of solid particles and maintained at coking temperatures of about 450° C. and 650° C., wherein there is produced a vapor phase product, including normally liquid hydrocarbons, and where coke is deposited on the solid particles;

(b) passing the vapor phase product to said scrubbing zone;

(c) passing the solid particles, with coke deposited thereon, downwardly through the coking zone, through the stripping zone, wherein they exit said the fluid coking reactor and are passed into said heating zone which contains a fluidized bed of solid particles and which is operated at a temperature greater than that of the coking zone;

(d) recycling at least a portion of the solids from the heating zone to the coking zone; and (e) introducing a stream comprised of one or more C$_2$ to C$_{10}$ paraffins into the heated solids passing from said heating zone to said coking zone, wherein they are contacted with the heated solids which causes said paraffins to become dehydrogenated to the respective olefins.

2. The process of claim 1 wherein the paraffin stream which is introduced into the solid particles passing from the heating zone to the coking zone are $C_2$ to $C_6$ paraffins.

3. The process of claim 2 wherein the coking zone is operated at a temperature from about 450° C. to 650° C. and a pressure from about 0 to 150 psig.

4. The process of claim 1 wherein the chargestock is selected from the group consisting of heavy and reduced petroleum crudes, petroleum atmospheric distillation bottoms, petroleum vacuum distillation bottoms, pitch, asphalt, bitumen, and liquid products derived from a coal liquefaction process.

5. The process of claim 4 wherein the chargestock has a Conradson carbon content of about 5 to 40 wt. %.

6. The process of claim 1 wherein a portion of the solid particles in the heating zone is passed to a gasification zone which is operated at a temperature greater than that of the heating zone.

7. The process of claim 6 wherein the paraffin stream which is introduced into the solid particles passing from the heating zone to the coking zone are $C_2$ to $C_6$ paraffins.

8. The process of claim 6 wherein the coking zone is operated at a temperature from about 450° C. to 650° C. and a pressure from about 0 to 150 psig.

9. The process of claim 6 wherein the chargestock is selected from the group consisting of heavy and reduced petroleum crudes, petroleum atmospheric distillation bottoms, petroleum vacuum distillation bottoms, pitch, asphalt, bitumen, and liquid products derived from a coal liquefaction process.

10. The process of claim 9 wherein the chargestock has a Conradson carbon content of about 5 to 40 wt. %.

11. The process of claim 1 wherein an effective amount of metal selected from Groups IA, IIA, VA, VIA, VIIA, and VIIIA of the Periodic Table of the Elements is incorporated into said integrated process in the coking zone.

12. The process of claim 11 wherein the metal is selected from the group consisting of potassium, calcium, vanadium, nickel, and iron.

* * * * *